US012722131B2

(12) United States Patent
Sinha et al.

(10) Patent No.: US 12,722,131 B2
(45) Date of Patent: Sep. 1, 2026

(54) DYNAMICALLY BALANCED AGGLOMERATED POWDER SPRAY DRYING SYSTEM AND METHOD THEREOF

(71) Applicant: Sigachi Industries Limited, Hyderabad (IN)

(72) Inventors: Amit Raj Sinha, Hyderabad (IN); Monika Tomar, Bharuch (IN); Kumar Rohit Raj, Bharuch (IN)

(73) Assignee: SIGACHI INDUSTRIES LIMITED, Hyderabad (IN)

( * ) Notice: Subject to any disclaimer, the term of this patent is extended or adjusted under 35 U.S.C. 154(b) by 19 days.

(21) Appl. No.: 18/528,200

(22) Filed: Dec. 4, 2023

(65) Prior Publication Data

US 2025/0001377 A1 Jan. 2, 2025

(30) Foreign Application Priority Data

Jun. 27, 2023 (IN) ............................. 202341043067

(51) Int. Cl.
*B01J 2/04* (2006.01)
*A61J 3/10* (2006.01)
*A61K 9/20* (2006.01)

(52) U.S. Cl.
CPC . *B01J 2/04* (2013.01); *A61J 3/10* (2013.01); *A61K 9/2095* (2013.01)

(58) Field of Classification Search
None
See application file for complete search history.

(56) References Cited

U.S. PATENT DOCUMENTS

2015/0246333 A1* 9/2015 Nielsen ..................... F26B 3/08 264/6

FOREIGN PATENT DOCUMENTS

EP 1161940 A1 * 12/2001 ........... A61K 9/2095

* cited by examiner

*Primary Examiner* — Christopher T Schatz
(74) *Attorney, Agent, or Firm* — DITTHAVONG, STEINER, & MLOTKOWSKI

(57) ABSTRACT

A spray dryer system for transforming a liquid-solid suspension feed solution into a desirable output product. A drying chamber having a controller device that is configured to obtain a first input associated with properties of a desirable output product, obtain a second input associated with critical quality attributes (CQAs) of the desirable output product, and obtain a third input associated with operational process variables of the drying chamber to generate the desirable output product. The drying chamber is adapted to receive dispersed droplets of a feed solution. The dispersed droplets are generated based on the obtained properties, obtained CQAs, and obtained operational process variables, and thereby transforms the dispersed droplets into dry particles by drying the dispersed droplets by supplying a continuous flow of the air for drying. The dry particles are generated based on the obtained properties, obtained CQAs, and obtained operational process variables.

7 Claims, 15 Drawing Sheets

DYNAMICALLY BALANCED AGGLOMERATED POWDER SPRAY DRYING SYSTEM AND METHOD THEREOF

RELATED APPLICATION

This application claims priority to Indian Patent Application No. IN 202341043067, filed Jun. 27, 2023, the contents of which are hereby incorporated in its entirety.

TECHNICAL FIELD

The present invention relates to spray drying, more particularly, the present invention relates dynamically balanced agglomerated powder spray drying technology (DAPO-Bal) for conventional and co-processed excipients for balanced and most critical tablet properties.

BACKGROUND

Spray dryers have been used for a number of years to produce powdered milk, powdered chalk, powder for cosmetics, and other similar powdered products from feed solutions consisting of solids dissolved, dispersed or suspended in water. Essentially, all spray dryers are comprised of a source of a continuous flow of hot air; a drying chamber; an atomizing system; and a powder recovery system, with the air source typically including an air supply fan, an air heater and an air distribution system, and with the powder recovery system typically including a powder separation system and an exhaust air flow system. The function of the air source is to cause heated air, flowing continuously at a relatively high velocity, to be introduced into the drying chamber while the feed solution is being dispersed as small droplets into the air flow by the atomizing system.

Spray Drying is the most common of the free-flowing powder manufacturing technology of today. It consists of atomizing a liquid, solution, emulsion or suspension into a hot gas medium to dry and transform it into particles in a one-step operation, without any external interventions. As a powder manufacturing technique, Spray Dryer allows modification of process parameters towards better and more desirable powder properties, which in effect result in improved final product tablet or hard filling into capsule formulation.

In general, there are three methods are used to manufacture tablet—(a) Direct Compression, (b) Dry Granulation, and (c) Wet Granulation.

Direct compression is the most effective and widely used manufacturing process, which involves only blending with the desired Active Pharmaceutical Ingredient and other relevant Excipients, going in for Blending and thereafter tableting. A directly compressible adjuvant should have a particle size equivalent to the active ingredients present in the formulation. The particle size distribution should be consistent from batch to batch. Reproducible particle size distribution is necessary to achieve uniform blending with the active ingredients in order to avoid segregation of API and Excipient. However, this results in a lot of thrust on flow properties, consistency, and range of parameters like bulk density etc. Poor flowability might result in unacceptable low content uniformity in tablet to tablet.

Wet granulation method is old and widely used to manufacture tablet formulation. Wet Granulation method consists of various steps. It's a lengthy process in comparison to direct compression, it is also a more tedious process and involves higher costs. Dry granulation method is also used to manufacture tablet, it is compatible with few tablets formulation but not suitable for all tablets.

Spray dried microcrystalline cellulose is a highly consumed binder-filler. It is used to make table by direct compression, wet and dry granulation. Microcrystalline Cellulose, due to its inherent characteristics, inert nature, good binding, and self-disintegrating and self-lubricant properties finds wide usage as an Excipient of choice for most of the Tableting processes. However, with the increasing number of new drugs, and typical physicochemical and stability needs, there is a growing pressure on formulators to look at innovative co-processed excipients, to achieve the desired set of functionalities into one excipient.

There is however an inherent need to be able to Dynamically balance all the properties viz. the Critical Quality Attributes like Bulk density, Texture, Particle size, moisture content, porosity, among others and Critical Process Parameters like temperature, feed parameters, air distribution system. This once done would produce powder that aligned to the need of the Oral Solid Dosage (OSD) industries. This powder would in turn positively impact and control drug degradation, microbial contamination and growth, tablet hardness, friability, etc.

SUMMARY

The present invention relates to dynamically tuning in feed characteristics, operating conditions for a specific spray dryer design to be able to control particle morphology, density, particle size and distribution, stickiness and moisture, such that the most desired final tablet properties are achieved post tableting.

Many conventional and co-processed excipients are produced via the Spray drying route. This invention relates to the use of dynamically balanced agglomerated powder spray drying technology (DAPO-Bal™) technology, which would be a dynamic mix of critical quality attributes (CQA) of powder, critical process parameters (CPP) whilst spray drying to get the most balanced critical and desirable tablet properties. The preferred excipient being microcrystalline cellulose and its co-processed excipient HiCel™ HFS being a combination of microcrystalline cellulose, mannitol and colloidal silicon dioxide.

Accordingly, an objective of the present invention to manufacture free flowing powder using DAPO-Bal technology, evaluate a dynamic mix of Critical Quality Attributes of powder and Critical Process Parameters.

Another objective of the present invention to manufacture co-processed powder using DAPO-Bal technology. The Co-processed powder thus made would be highly supported where API have poor flowability, compressibility and are hygroscopic in nature.

To achieve the same, the present invention provides a dynamically balanced agglomerated powder spray drying technology (DAPO-Bal) for conventional and co-processed excipients for balanced and most critical tablet properties.

BRIEF DESCRIPTION OF DRAWINGS

Preferred representations of the non-invasive system of the present invention are described in detail below with reference to the drawings wherein:

FIGS. 3A-1, 3A-2, 3B-1 and 3B-2 show the Flowability parameters like FFC values, Angle of repose, as a factor of outlet air temperature and moisture of HiCel 90M and HiCel HFS 90M, in accordance with the present invention.

DESCRIPTION OF EMBODIMENTS

Figure 1:
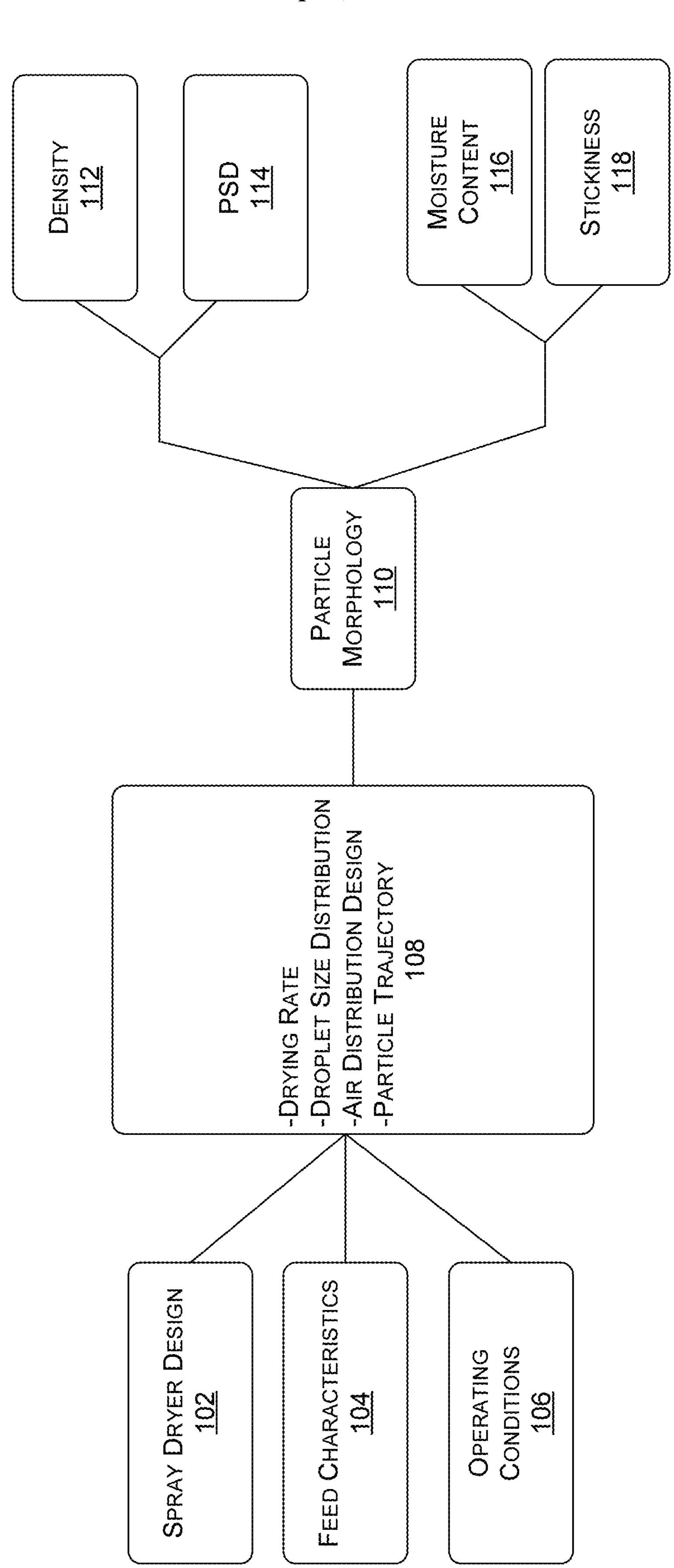
FIG. 1 is the Stimulus Response diagram of various inputs and their corresponding response on the Critical Quality Attributes (CQA), in accordance with the present invention.

The word “exemplary” or “embodiment” is used herein to mean “serving as an example, instance, or illustration.” Any implementation or aspect described herein as “exemplary” or as an “embodiment” is not necessarily to be construed as preferred or advantageous over other aspects of the disclosure. Likewise, the term “aspects” does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms “a,” “an,” and “the” include plural referents unless the context clearly dictates otherwise. Ranges may be expressed herein as from “about” one particular value, and/or to “about” another particular value. When such a range is expressed, another embodiment includes from the one particular value and/or to the other particular value. Similarly, when values are expressed as approximations, by use of the antecedent “about,” it will be understood that the particular value forms another embodiment. It will be further understood that the endpoints of each of the ranges are significant both in relation to the other endpoint, and independently of the other endpoint.

“Optional” or “optionally” means that the subsequently described event or circumstance may or may not occur, and that the description includes instances where said event or circumstance occurs and instances where it does not.

Throughout the description and claims of this specification, the word “comprise” and variations of the word, such as “comprising” and “comprises,” means “including but not limited to,” and is not intended to exclude, for example, other components, integers or steps. “Exemplary” means “an example of” and is not intended to convey an indication of a preferred or ideal embodiment. “Such as” is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

The foregoing objects of the invention are accomplished and the problems and shortcomings associated with the prior art techniques and approaches are overcome by the present invention as described below in the preferred embodiment.

The invention provides detailed parameters and controls that can have a positive effect on the powder being spray dried and thereafter resulting in most desired tablet properties. The Powder parameters like Moisture content, Particle size distribution, Stickiness and Bulk Density have been measured and quantified as a function of suspension properties, Spray Dryer Operations parameters like Flow rate & Inlet Air Temperature of Hot Air, The Feed flow rate, feed concentration and Atomiser Speed. The Stimulus Response Diagram indicating the input and the relevant output parameters is brought out at FIG. 1. The Product in this case is Microcrystalline Cellulose (MCC).

Another embodiment of invention also provides Mechanistic Model for maximizing product quality for Co-processed Excipients considering parameters brought out in Para above. The co-processed Excipient in this case would be a co-processed admixture of Binder, Sugar Alcohol, and Lubricant as HiCel™ HFS, but not limited to these categories of Excipient or ratios as brought out in HiCel™ HFS or any other co-processed excipients.

Figure 5:
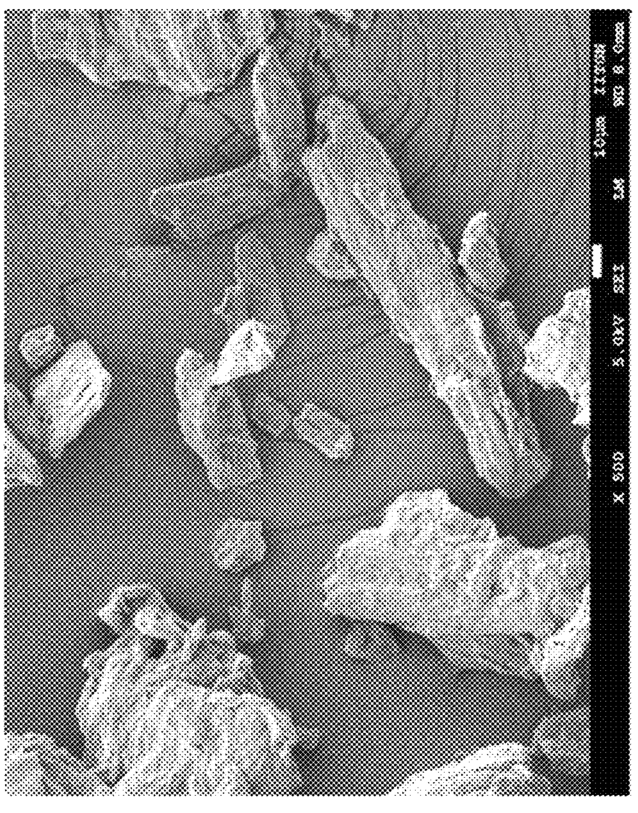
FIG. 5 SEM Image of HiCel™ 90M(Microcrystalline cellulose) manufactured under most desirable conditions as per FIG. 2, in accordance with the present invention.
Figure 7:
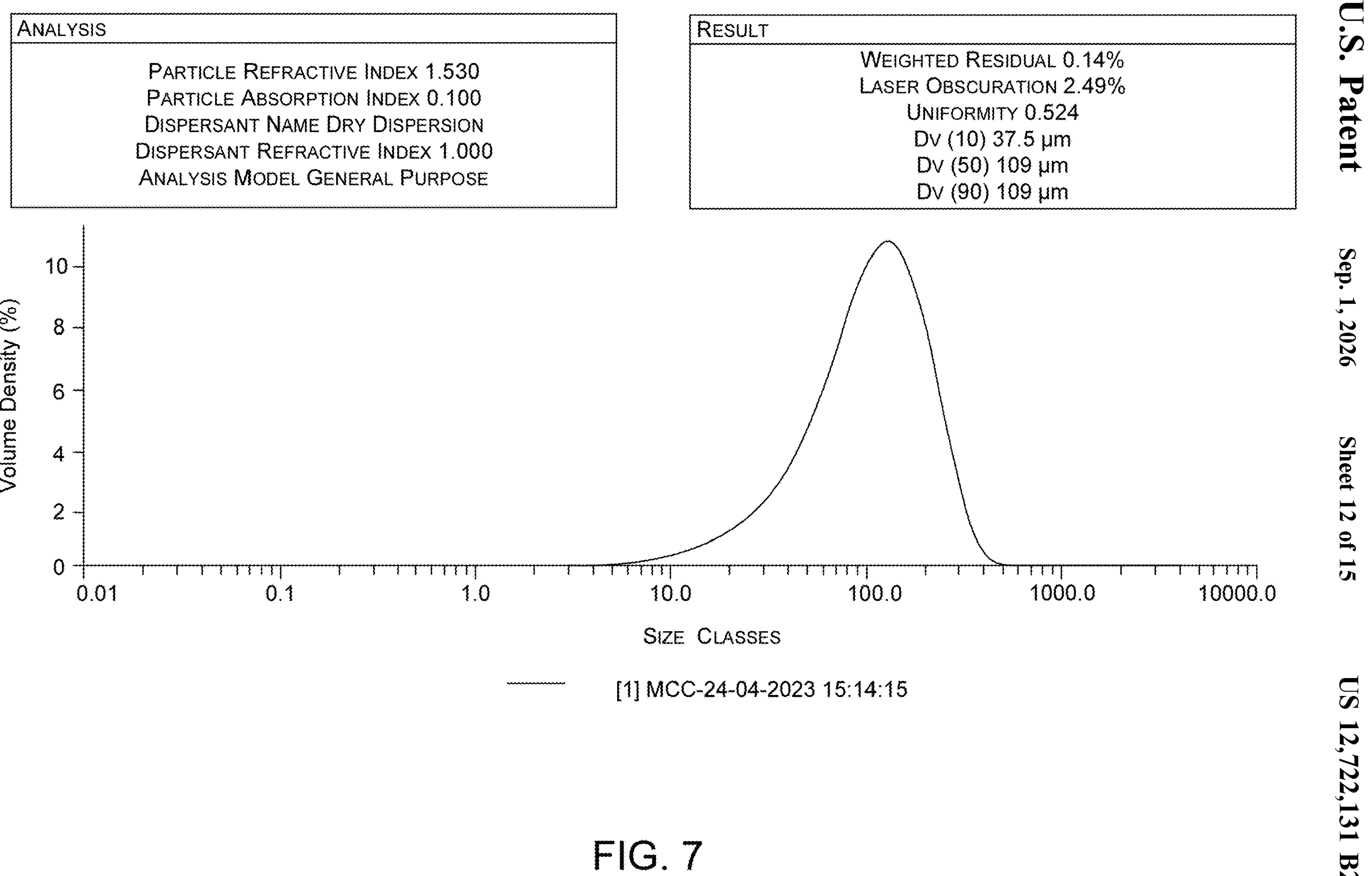
FIG. 7 Shown PSD graph of HiCel™ 90M(Microcrystalline cellulose) manufactured under most desirable conditions as per FIG. 2, in accordance with the present invention.
Figure 8:
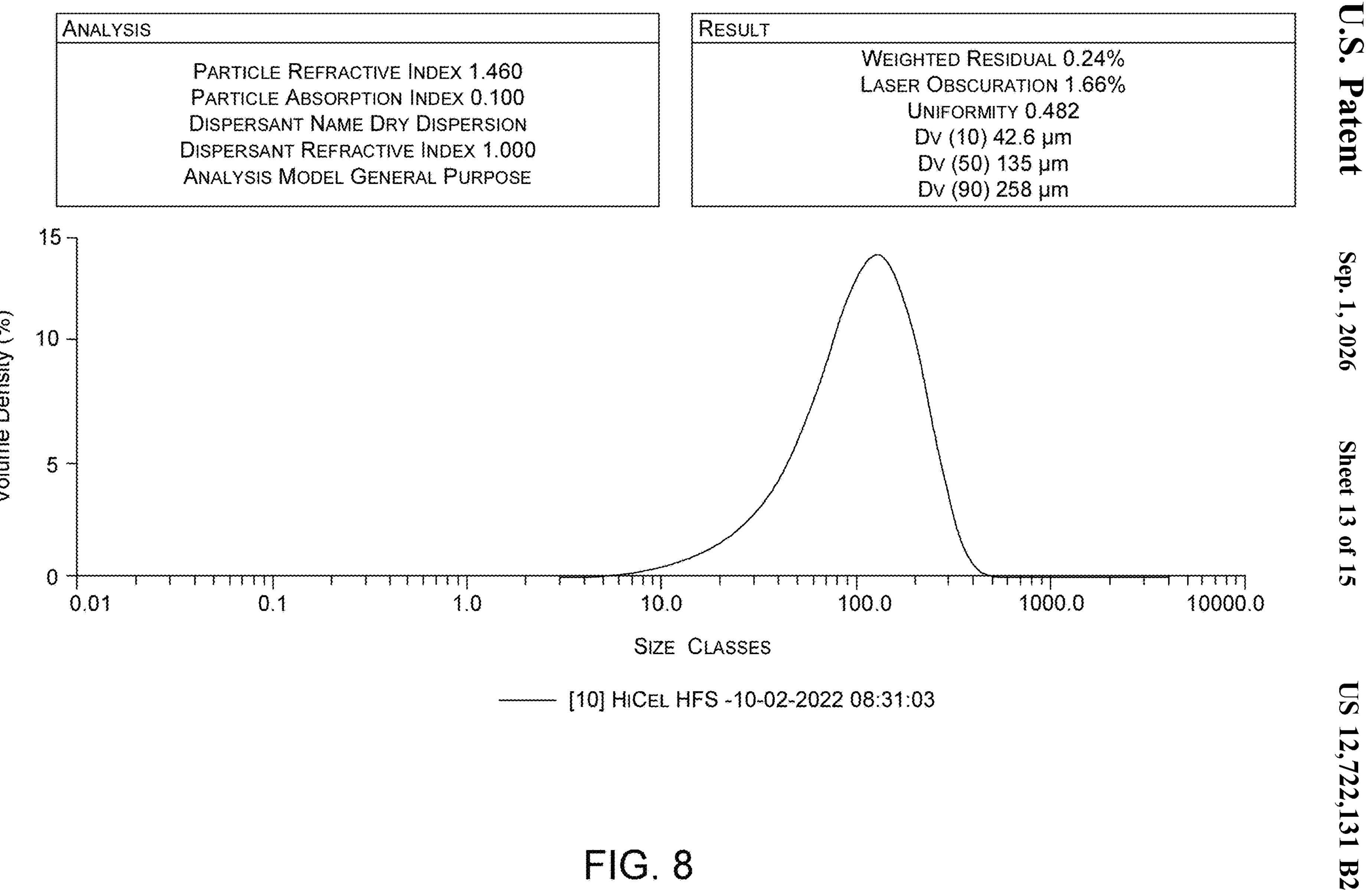
FIG. 8 Shown PSD graph of MCC co-processed HiCel™ HFS (MCC Co-processed being composition MCC, Colloidal silicon dioxide and Mannitol) manufactured under most desirable conditions as per FIG. 2, in accordance with the present invention.

In accordance with the present invention, FIG. 3 brings out the direct co-relation between the moisture levels and Outlet Air temperature of the Spray Dried Powder (in this case MCC) and the Angle of repose. The moisture content in this case being measured by Oven dry method at controlled temperature for a specific period. For this product, a combination of Moisture content and Water activity parameters have been studied to adequately control the shelf life, texture, agglomeration, and microbial growth detailed data mentioned into table 1A and 1B. This has been brought out at FIGS. 4 & 5. It has been seen that as the moisture level rises, the average primary particles in an agglomerate goes higher, thus adversely affecting the flowability, which again is evident from the increased angle of repose.

TABLE 1A

| Loss on drying (%) | Flowability (Angle of repose°) | Flowability description | Flowability Numerically (ffc value) |
|---|---|---|---|
| 7% | 44-46 | Very Cohesive | 1 |
| 5% | 41-43 | Cohesive | 2 |
| 4% | 38-40 | Easily flowing | 4 |
| 2% | 36-37 | Normal flowing | 7 |
| 1% | 35-36 | Free flowing | 12 |

TABLE 1B

| Loss on drying (%) | Water Activity | Microbial growth |
|---|---|---|
| 7% | 1.023 | High |
| 5% | 0.856 | Medium |
| 4% | 0.410 | Medium |
| 2% | 0.210 | Low |
| 1% | 0.046 | Low |

Tables 2A and 2B brings out the Particle Size Distribution (PSD) measured by Laser Diffraction which indicates not only the mean particle size, but also other parameters like Size Dispersion, particle agglomeration. It also brings to conclusion that Spray Dried Powder size and distribution are straightly related to the droplet size and distribution, which are again a factor of Suspension feed properties and Spray Dryer design (Atomizer type).

Table 2A brings out the Particle Size Distribution (PSD) measured by Laser Diffraction which indicates correlation between Particle mean size and moisture content (HiCel 90M). It may be noted that Loss on Drying parameters are also a function of outlet air temperature too.

TABLE 2A

| Loss on drying (%) | PSD carried out using with dry dispersion method (Atomizer RPM at 11,000) Trial 1 | Trial 2 | Trial 3 | Trial 4 | Trial 5 | Average |
|---|---|---|---|---|---|---|
| | D50 (μm) | | | | | |
| 7% | 134 | 134 | 137 | 137 | 133 | 135 |
| 5% | 122 | 120 | 125 | 123 | 120 | 122 |
| 4% | 104 | 108 | 113 | 118 | 102 | 109 |
| 2% | 93 | 94 | 100 | 102 | 101 | 98 |
| 1% | 86 | 87 | 95 | 92 | 90 | 90 |

Table 2B brings out the Particle Size Distribution (PSD) measured by Laser Diffraction which indicates correlation between Particle mean size and moisture content (HiCel HFS 90M). It may be noted that Loss on Drying parameters are also a function of outlet air temperature too.

TABLE 2B

| Loss on drying (%) | PSD carried out using with dry dispersion method (Atomiser RPM at 11,000) Trial 1 | Trial 2 | Trial 3 | Trial 4 | Trial 5 | Average |
|---|---|---|---|---|---|---|
| | D50 (μm) | | | | | |
| 7% | 166 | 164 | 160 | 154 | 156 | 160 |
| 5% | 150 | 152 | 148 | 138 | 137 | 145 |
| 4% | 125 | 127 | 118 | 120 | 110 | 120 |
| 2% | 113 | 113 | 115 | 102 | 102 | 109 |
| 1% | 103 | 95 | 97 | 100 | 100 | 98 |

This is done, while keeping other parameters like Atomiser speed, suspension feed properties constant. It is evident that with an increased Loss on Drying %, the mean PSD goes up. The average number of particles in a Particle agglomerate increases, as the moisture goes up and this factor is evident from the Table 2A and 2B.

In line with the present invention, another parameter directly affecting the finished Powder property is the Density. Though, the embodiment of this invention co-relates to only Bulk Density. There are other types of density which may be crucial for further tests like Real Density, Particle density. However, the two main parameters imposing on the density are a) Inter particle Porosity or Internal Pores; and b) Intra Particle Porosity or External Pores.

In another embodiment of this invention, the flow of powders or powder flowability index which could be Jenike Flow index, Hausner ratio or repose angle or slide angle was used. For the shear comfort of usage, and it being expensive for high value powder, the Jenike flow index was replaced with Hausner ratio and repose angle. Table 3 brings out co-relation between the powder flowability index parameters to that of Input Feed parameters, Air Flow and temperature. In terms of output parameters, it again shows direct co-relation to content uniformity in the final tablet.

Table 3A brings out the Pearsons Correlation coefficient between Moisture levels, Angle of Repose and the typical FFC Values for a fixed input feed parameter.

TABLE 3A

| | Outlet Air Temp (Degrees C.) | Moisture levels % | Angle of Repose (Degrees) | Typical FFC values |
|---|---|---|---|---|
| Outlet Air Temp (Degree C.) | 1 | | | |
| Moisture levels % | −0.997253699 | 1 | | |
| Angle of Repose (Degrees) | −0.917005223 | 0.92926578 | 1 | |
| Typical FFC values | 0.964067932 | −0.9686775 | −0.8976569 | 1 |

These values indicates that there is very strong correlation (positive or negative) between the parameters.

Table 3B—The general accepted norms for correlation coefficient (r) and its interpretation is given as under:

TABLE 3B

| Correlation Coefficient (r) | Interpretation |
|---|---|
| 0.00-0.10 | No correlation |
| 0.10-0.39 | Weak correlation |
| 0.40-0.69 | Moderate correlation |
| 0.70-0.89 | Strong correlation |
| 0.90-1.00 | Very strong correlation |

Figure 3A:
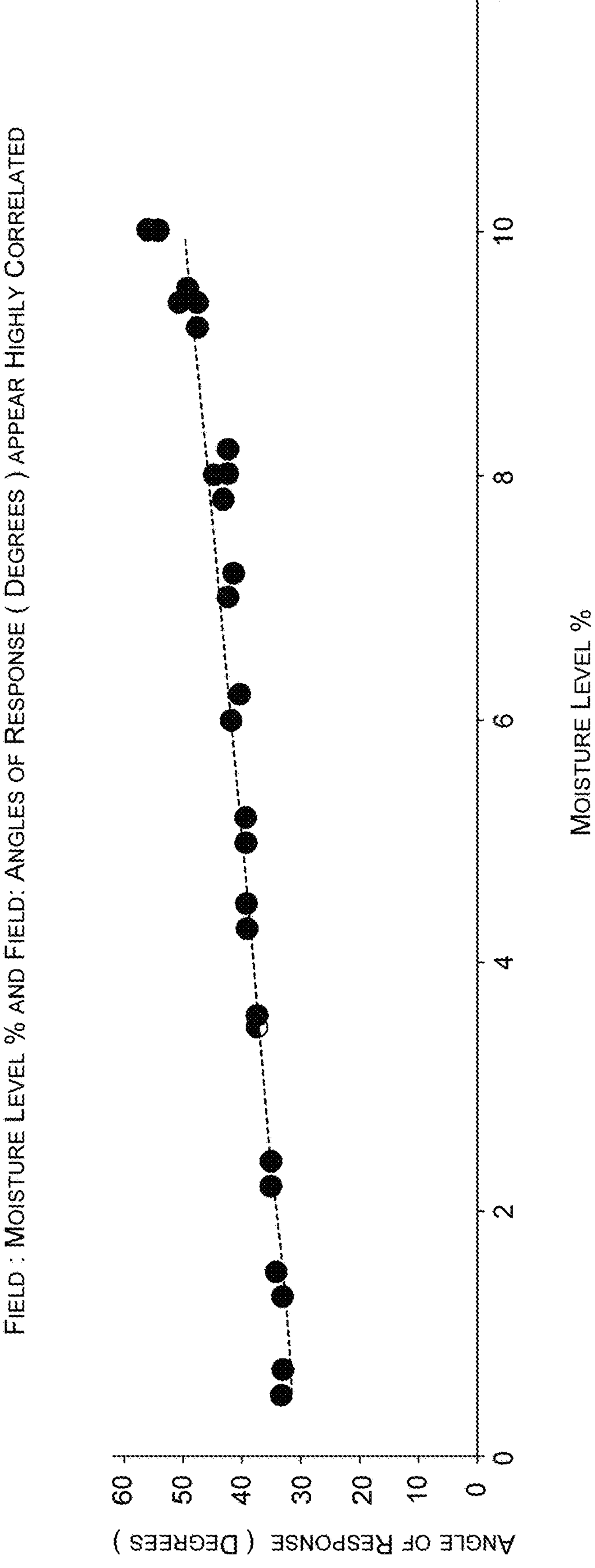
Figure 1:
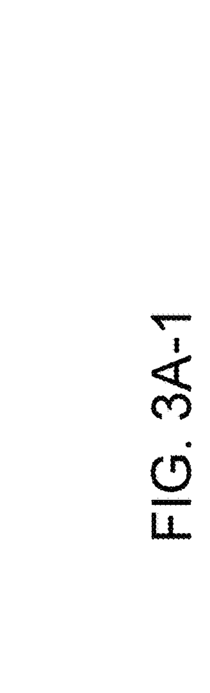
Figure 3A:
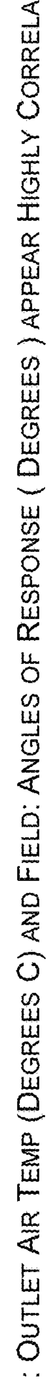
Figure 2:
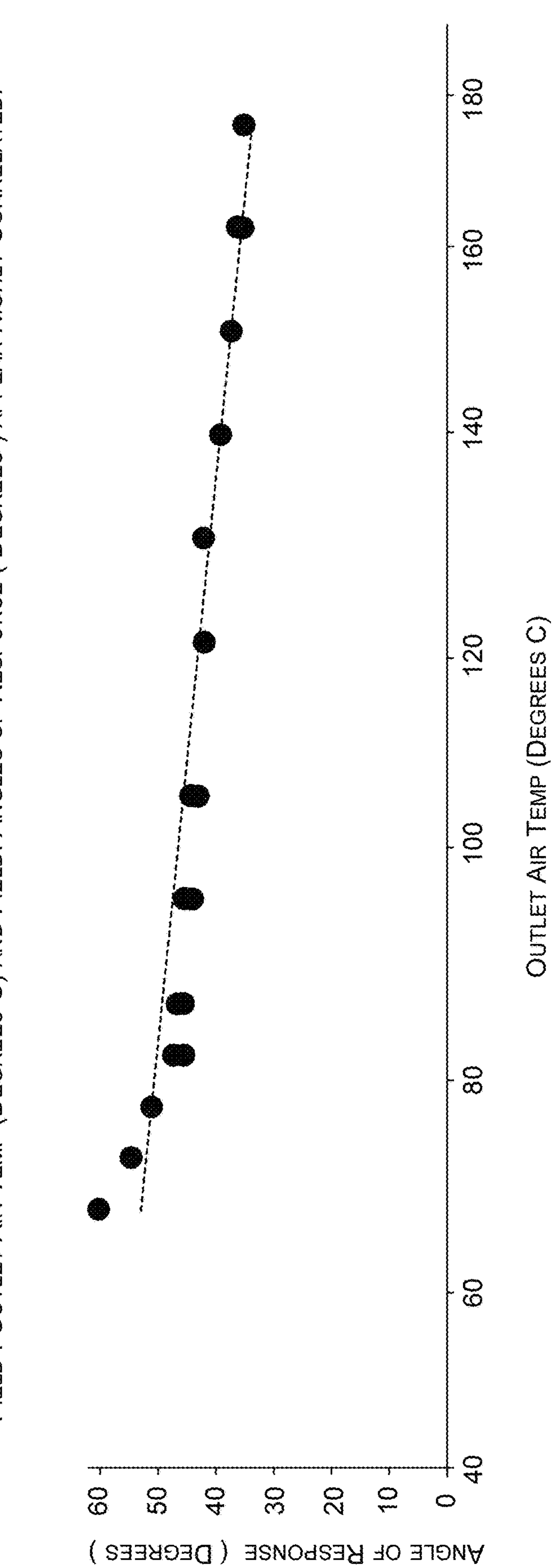

FIG. 3A-1, the moisture levels % and Angle of repose (Degrees) appear highly correlated (For a fixed input feed parameter) for HiCel 90M. In FIG. 3A-1, the Correlation Coefficient (r)—0.92926578.

Figure 2:
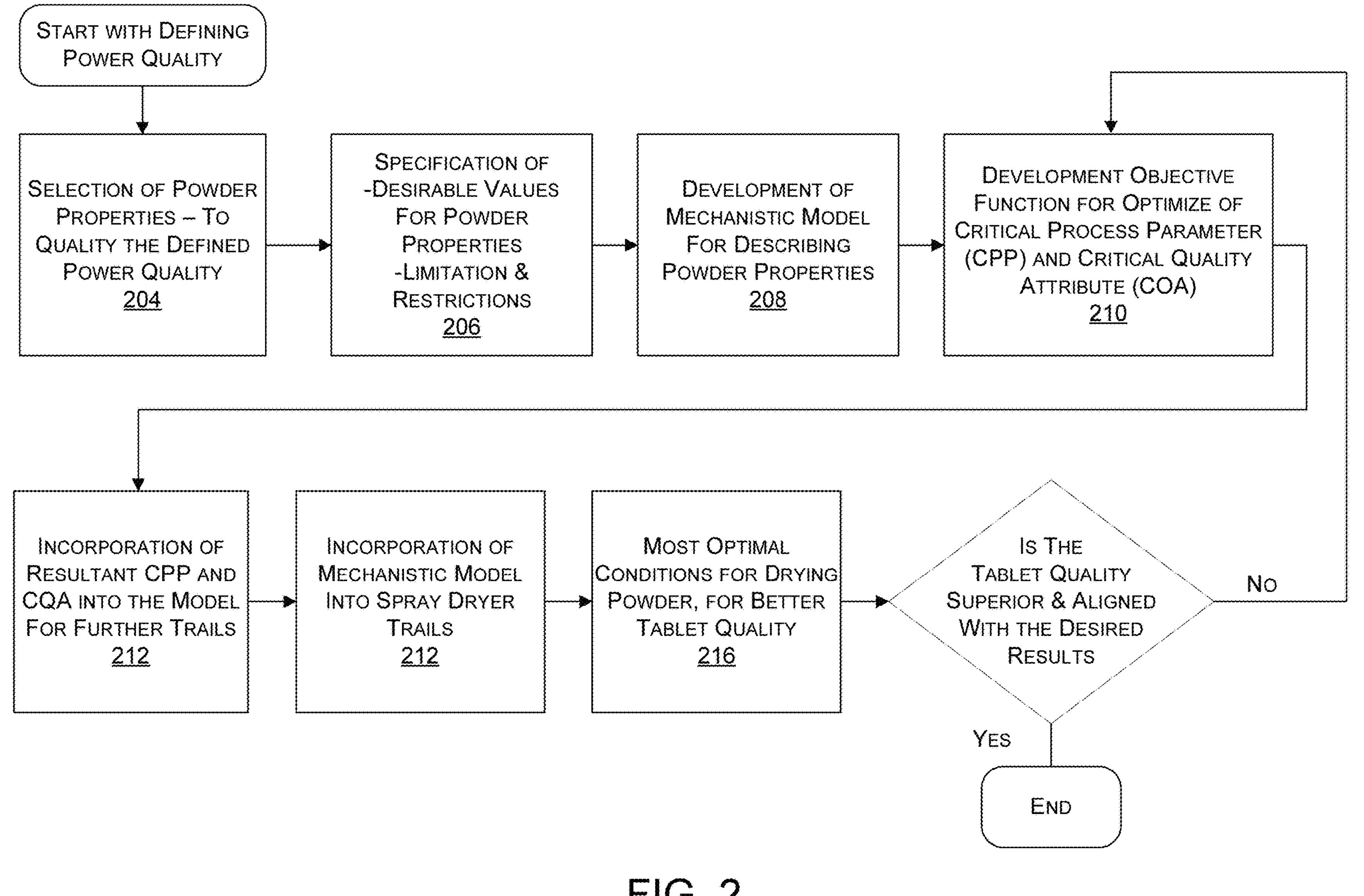
FIG. 2 is steps for optimising the various variables for the desired output, and thus the quality of the tablet being formed, in accordance with the present invention.

FIG. 3A-2 brings out co-relation between the powder flowability index parameters of HiCel 90M to that of Input Feed parameters, Air Flow and temperature. In FIG. 3A-2, the Correlation Coefficient (r)—−0.917005223.

Figures 1, 3B:
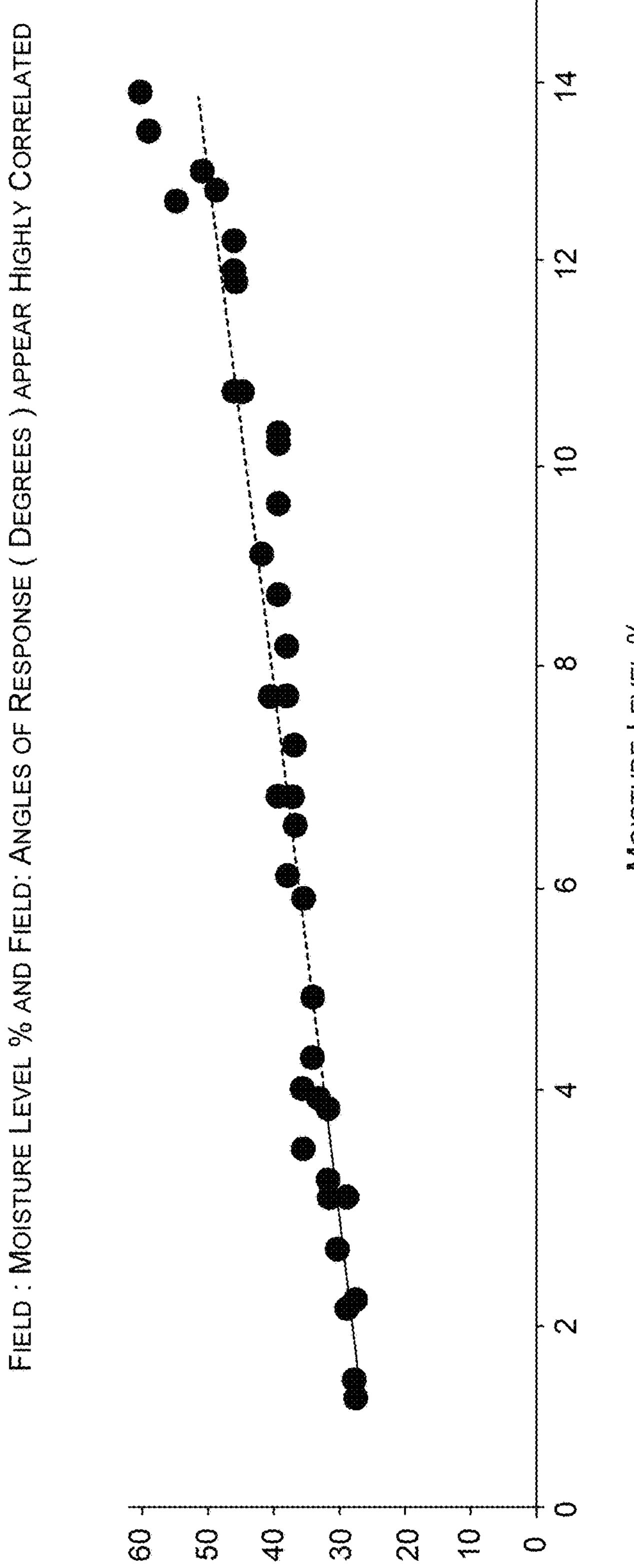
Figure 3B:
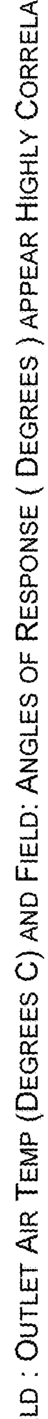
Figure 2:
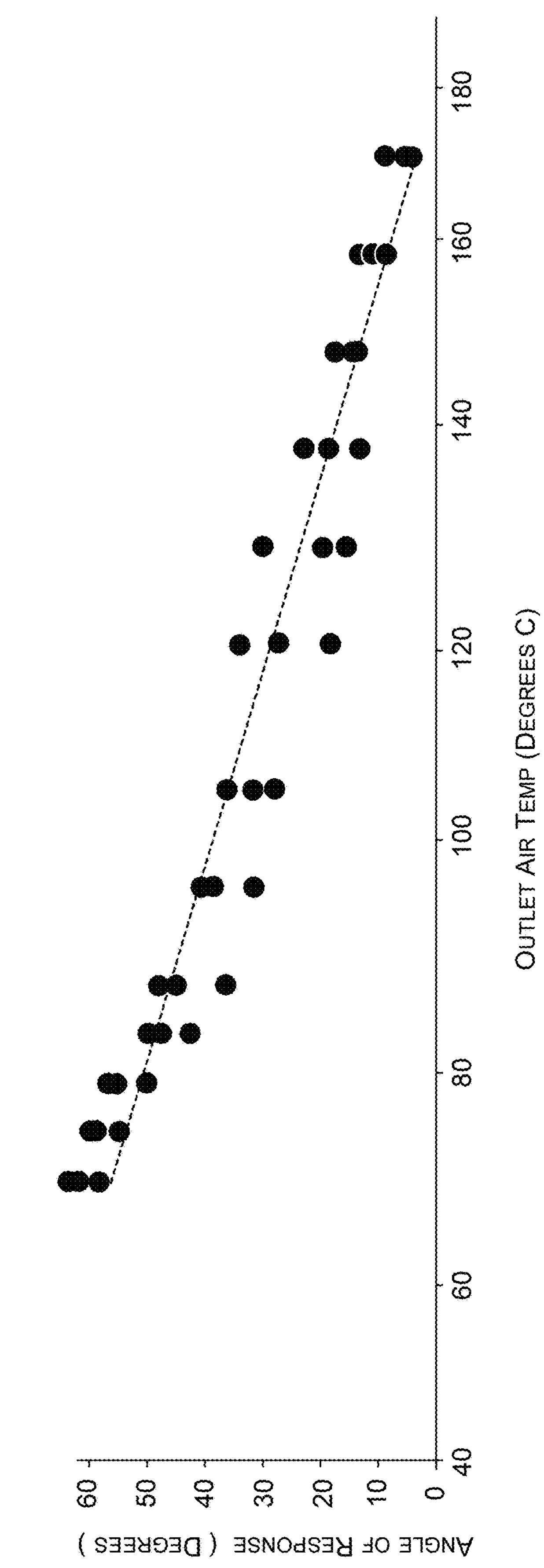
Figure 4A:
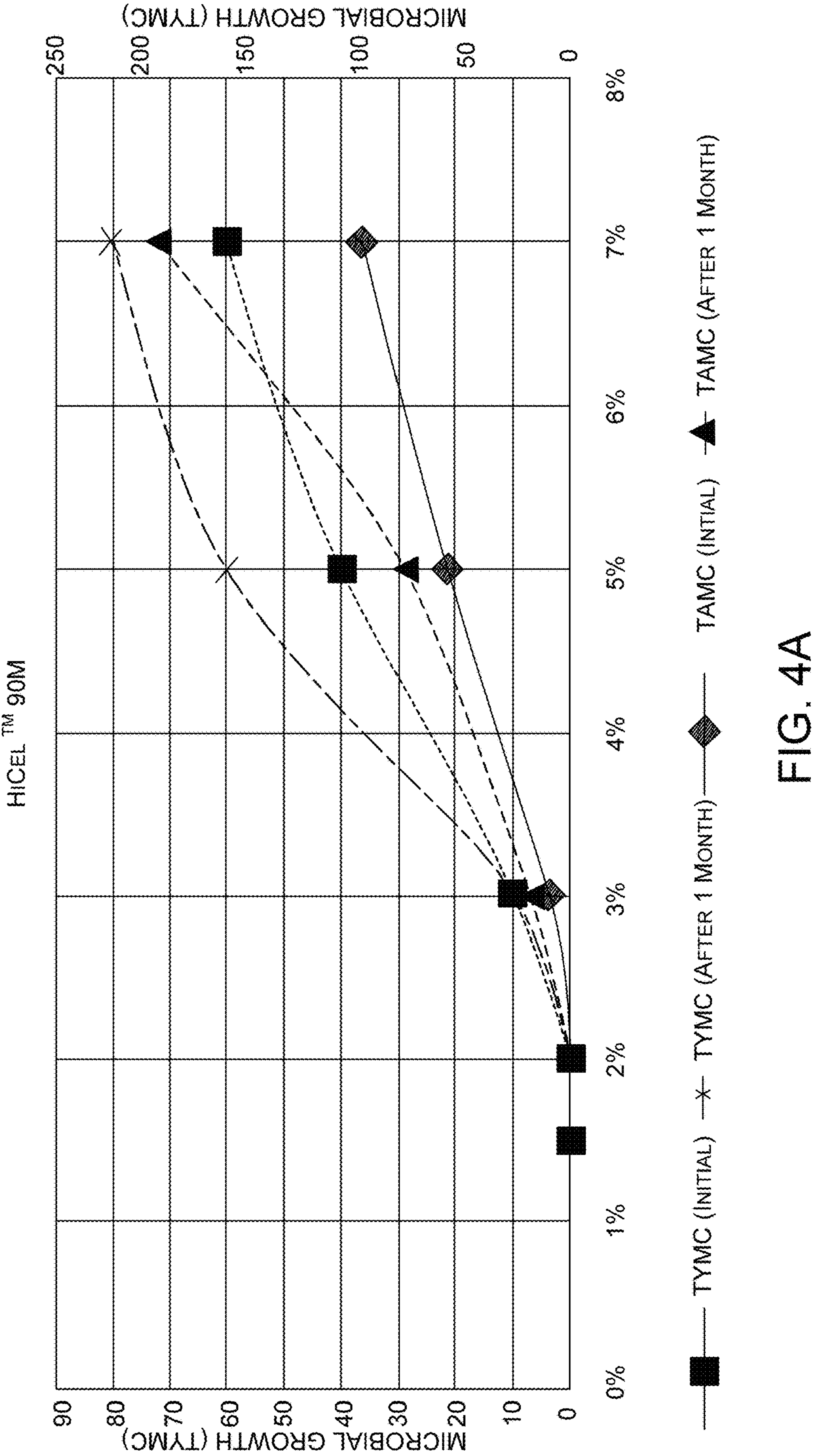
FIGS. 4A, 4B, 4C, and 4D are showing moisture content, texture, agglomeration, water activity and microbial growth for MCC HiCel 90M and HiCel HFS 90M, in accordance with the present invention.
Figure 4B:
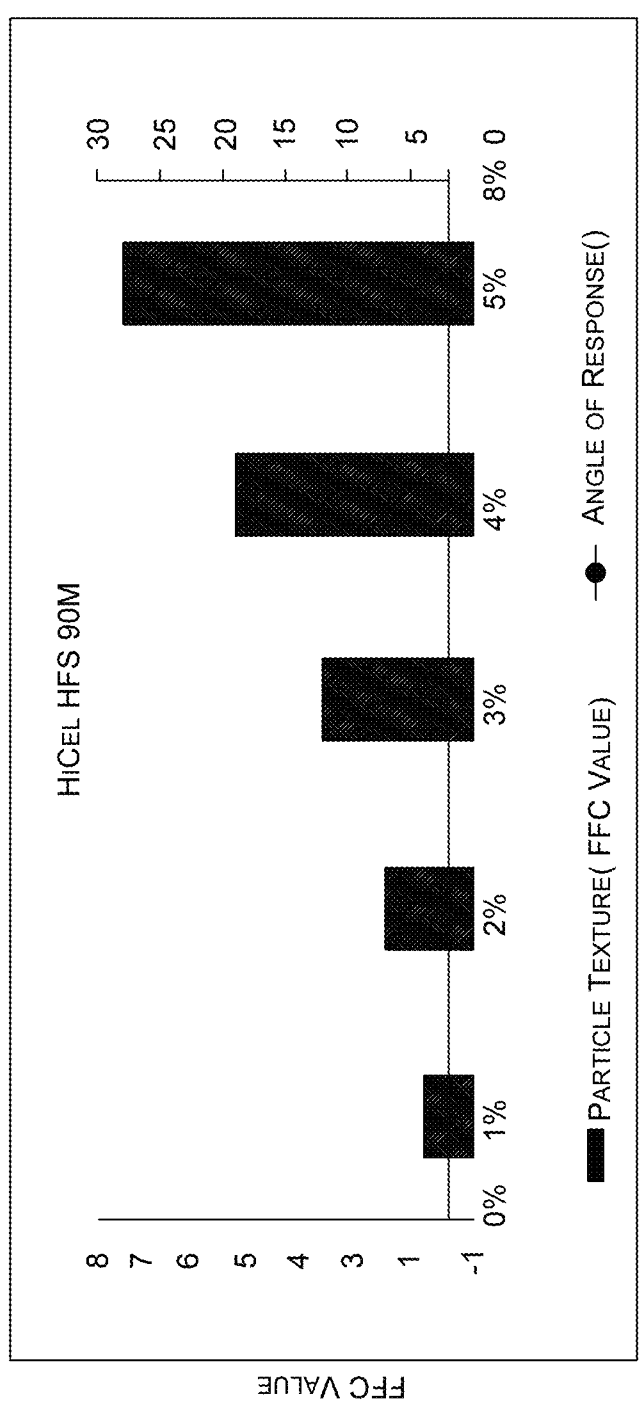
Figure 4C:
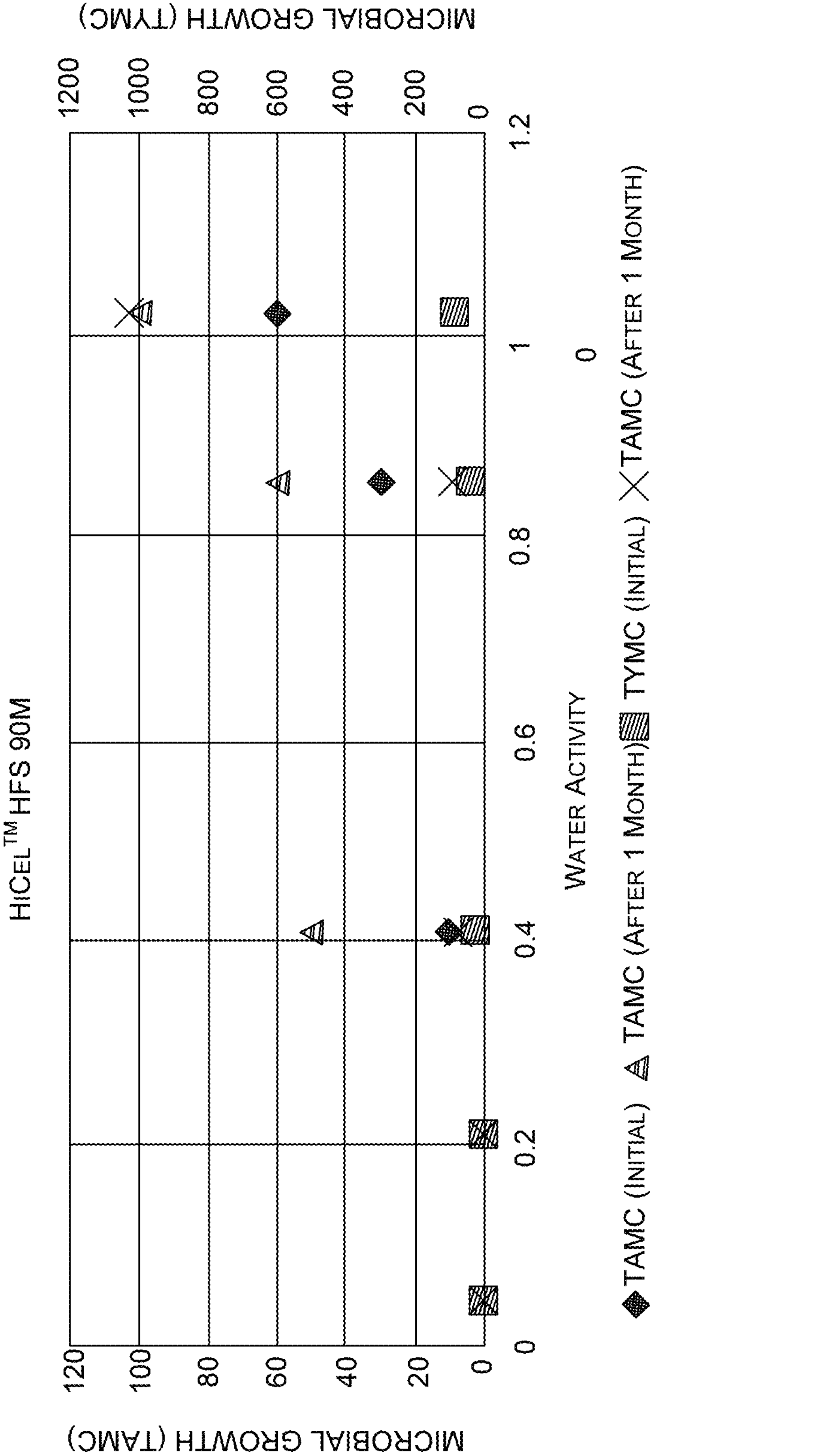
Figure 4D:
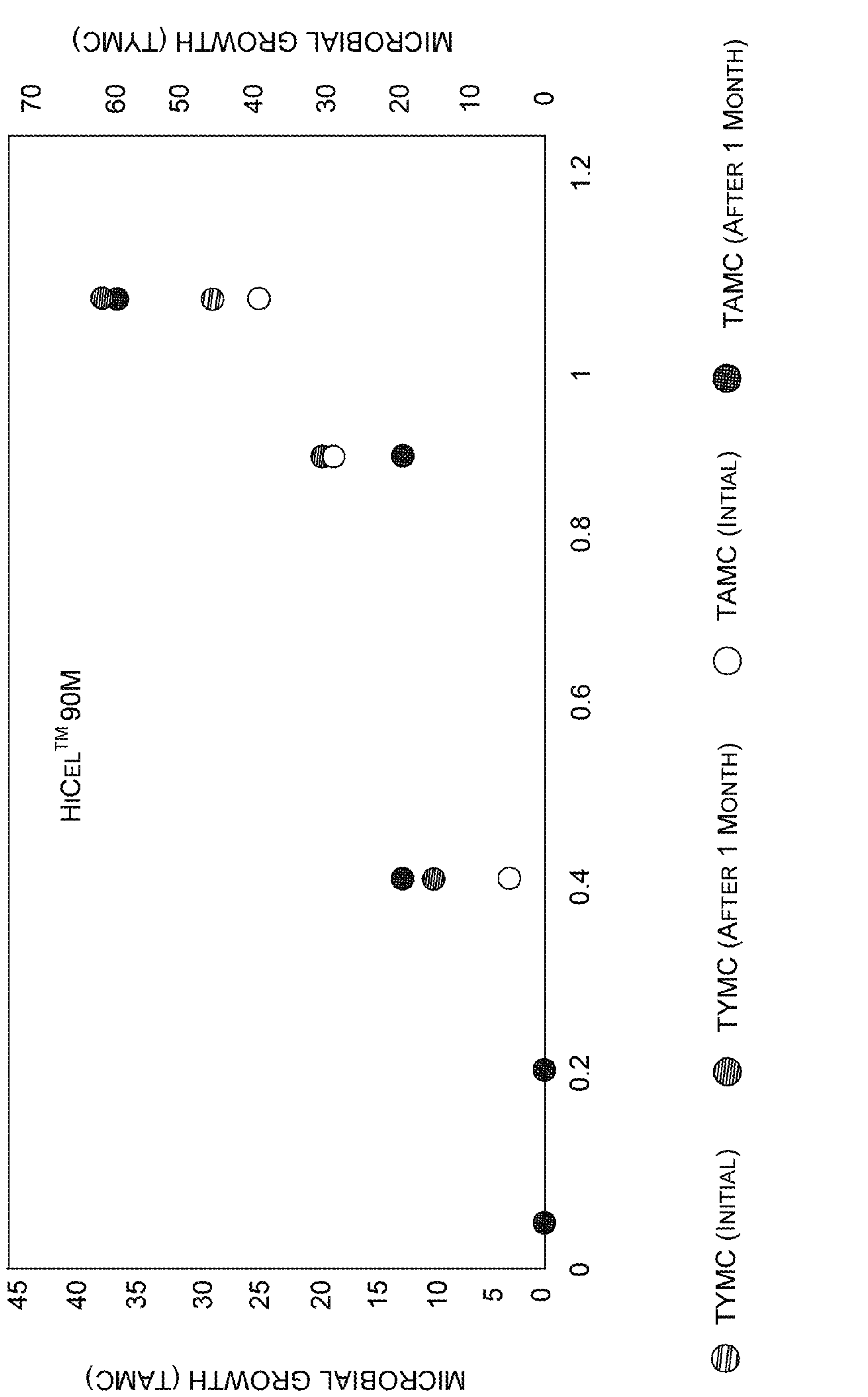
Figure 6:
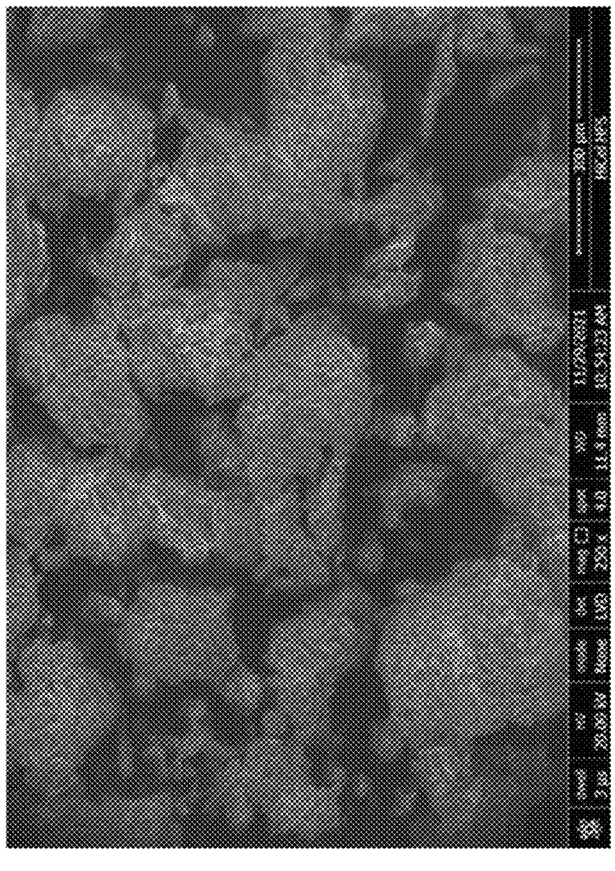
FIG. 6 SEM Image of HiCel™ HFS (MCC Co-processed being composition MCC, Colloidal silicon dioxide and Mannitol) manufactured under most desirable conditions as per FIG. 2, in accordance with the present invention.

FIG. 3B-1, the moisture levels % and Angle of repose (Degrees) appear highly correlated (For a fixed input feed parameter) for HiCel HFS. In FIG. 3B-1, the Correlation Coefficient (r)—0.933129.

FIG. 3B-2, the moisture levels % % and Outlet Air Temp (Degrees C.) appear highly correlated (For a fixed input feed parameter) for HiCel HF. In FIG. 3B-1, the Correlation Coefficient (r)—−0.963866892.

The Mechanistic model to control the Spray Dryer operation variables to obtain the desired product output has been strategized in FIG. 2. As a starting point, it becomes imperative to define the desirable product in the end application. In our case, the most desirable properties come out to be: tablet hardness, tablet disintegration time, friability, and content uniformity.

Once the Most desired product output properties have been finalized, we have worked out the powder quality, corresponding to this final product quality. Thus, Critical Quality Attributes (CQA), that best describe this quality have been brought out as: a moisture content, a particle size distribution, bulk density, a flowability index.

This powder quality is again a direct co-relation to the Spray Dryer operation conditions. The powder quality should be defined by the relationship between the operational process variable that best describe these properties. The Operational process variables or the Critical Process Parameters (CPP) are as: a feed flow rate, an inlet air temperature of hot air, a feed concentration, an atomizer speed.

In another embodiment of the invention the Mechanistic model as above was repeated for co-processed excipient HiCel™ HFS, and results were recorded. The principle of Factorial design was put into play, with two factors play i.e. Critical Quality Attributes (CQA) (A Level) and Critical Process Parameters (CPP) (B Level). The main idea of this design was to perform sets of experiments, considering all possible variations in factors. Here we have used $2^k$ factorial type (K factors at two levels). As there are only two levels, the response is evidently coming out to be linear in the range of study for this invention. The statistical model used for two levels of A and B would use the statistical model as below:

$$Y = \beta_0 + \beta_1 A + \beta_2 B + \beta_3 AB$$

Where,

Y: Estimate from the response variable $\beta_0$, $\beta_1$, $\beta_2$, $\beta_3$: Parameters A: Factor 1, Critical Quality Attributes (CQA)

B: Factor 2, Critical Process Parameters (CPP)

The outcome from the Mechanistic model of the invention can provide one or more benefits or advantages when utilized as a pharmaceutical excipient. This object of this invention can help the ingredient manufacturers tailor make their products to be suitable and beneficial to the Formulations company. The resultant tablets prepared from the ingredients with two factor control system displayed decreased friability, high compaction strength, lower Disintegration time (DT). Also, in the Tableting formulation, which contains ingredients from the said invention process get formed at a much lesser compaction force, the resultant wear and tear on the machines also decreases. In addition, improved yields can be obtained since fewer tablets will fail to reach the desired tablet strength.

Accordingly, a DAPO-Bal™ technology of transforming a liquid-solid suspension feed solution into a dry powder is provided. The technology includes supplying a continuous flow of the air required for drying, and heating the flow of drying air to a desired, relatively high temperature.

A drying chamber for receiving dispersed, small droplets of the feed solution and wherein the droplets are transformed into dry particles.

An air distribution system which relates to the air supply, and which directs the flow of drying air into the drying chamber so that the air flowing into the drying chamber has substantially uniform temperature and velocity profiles.

An atomizing system which forms the dispersed droplets of feed solid-liquid suspension solution into the flow of drying air as the drying air is introduced into the drying chamber.

The critical process parameters impacting the critical quality attributes and the correlation therein can be controlled and managed in real-time. Further, the outlet temperature impact on moisture content and thereby its correlation to flowability and hence the same can be controlled and managed in real-time.

Figure 9:
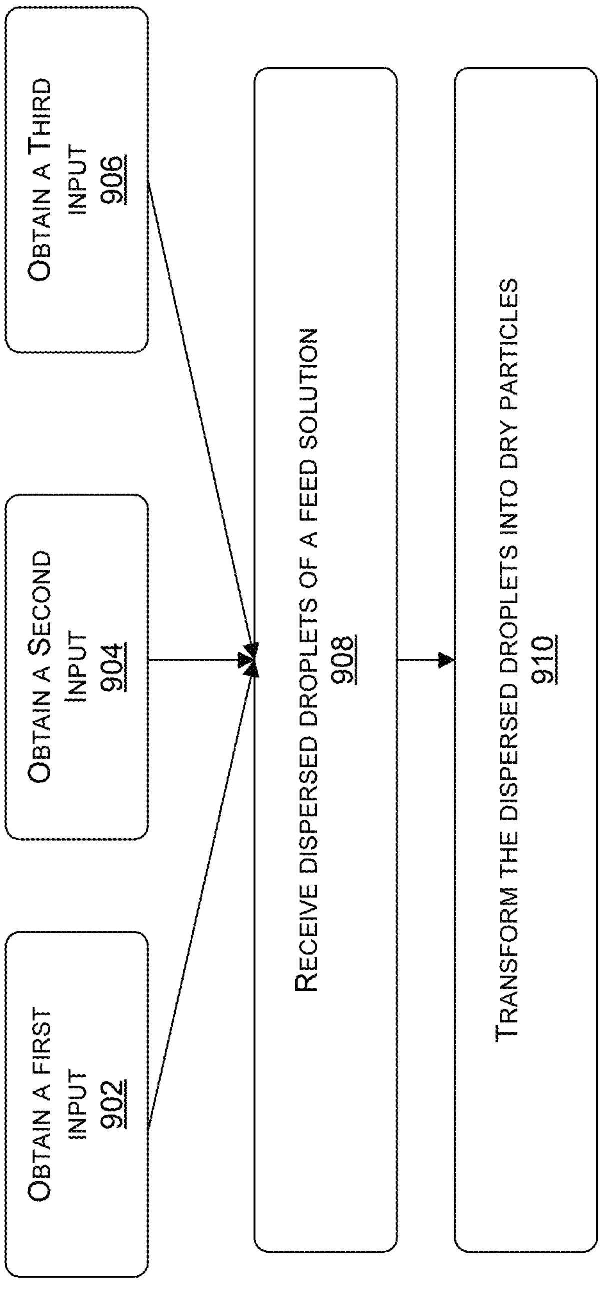
FIG. 9 illustrates a method for transforming a liquid-solid suspension feed solution into a desirable output product, in accordance with the present invention.

FIG. 9 illustrates a method for transforming a liquid-solid suspension feed solution into a desirable output product, in accordance with the present invention. The output product is a solid unit dosage form of medication with suitable excipients.

At step 902, at a controller device of a drying chamber obtains a first input associated with one or more properties of the desirable output product. The controller device controls the operations of the drying chamber to obtain the desirable output product.

At step 904, the controller device obtains a second input associated with one or more critical quality attributes (CQAs) of the desirable output product. In an exemplary embodiment, the one or more properties are associated with at least one of a hardness, a disintegration time, a friability, and a content uniformity.

At step 906, the controller device obtains a third input associated with one or more operational process variables of the drying chamber to generate the desirable output product. In an exemplary embodiment, the one or more critical quality attributes (CQAs) are associated with at least one of a moisture content, a particle size distribution, a stickiness, a bulk density, and a flowability index.

At step 908, the drying chamber receives dispersed droplets of a feed solution. The dispersed droplets are generated based on the one or more obtained properties, the one or more obtained CQAs, and the one or more obtained operational process variables. In an exemplary embodiment, the one or more operational process variables are associated with at least one of a feed flow rate, an inlet air temperature of hot air, a feed flow rate of the feed solution, a feed concentration of the feed solution, and an atomiser speed generating the dispersed droplets.

In an exemplary embodiment, the dispersed droplets of the feed solution are obtained from an automizer fluidly coupled to the drying chamber.

At step 910, the dispersed droplets are transformed, inside the drying chamber, into dry particles by drying the dispersed droplets by supplying a continuous flow of the air for drying. The dry particles are generated based on the one or more obtained properties, the one or more obtained CQAs, and the one or more obtained operational process variables.

In an exemplary embodiment, the continuous flow of the air for drying is supplied by an air distribution system coupled to the drying chamber, and wherein the air distribution system directs the flow of the drying air into the drying chamber with a uniform temperature and a uniform velocity.

In an exemplary embodiment, the continuous flow of the air for drying, entering into the drying chamber, is heated at a pre-determined temperature so that the heated air entering the drying chamber generates a heated gas atmosphere inside the drying chamber to transform the dispersed droplets into dry particles.

In an exemplary embodiment, the method also includes the step of obtaining the dry particles along with the air for drying at an outlet of the drying chamber.

In an exemplary embodiment, the method also includes the step of collecting the obtained dry particles at a collection chamber connected to the drying chamber. Further, this step also allows the obtained air for drying into atmosphere.

Figure 10:
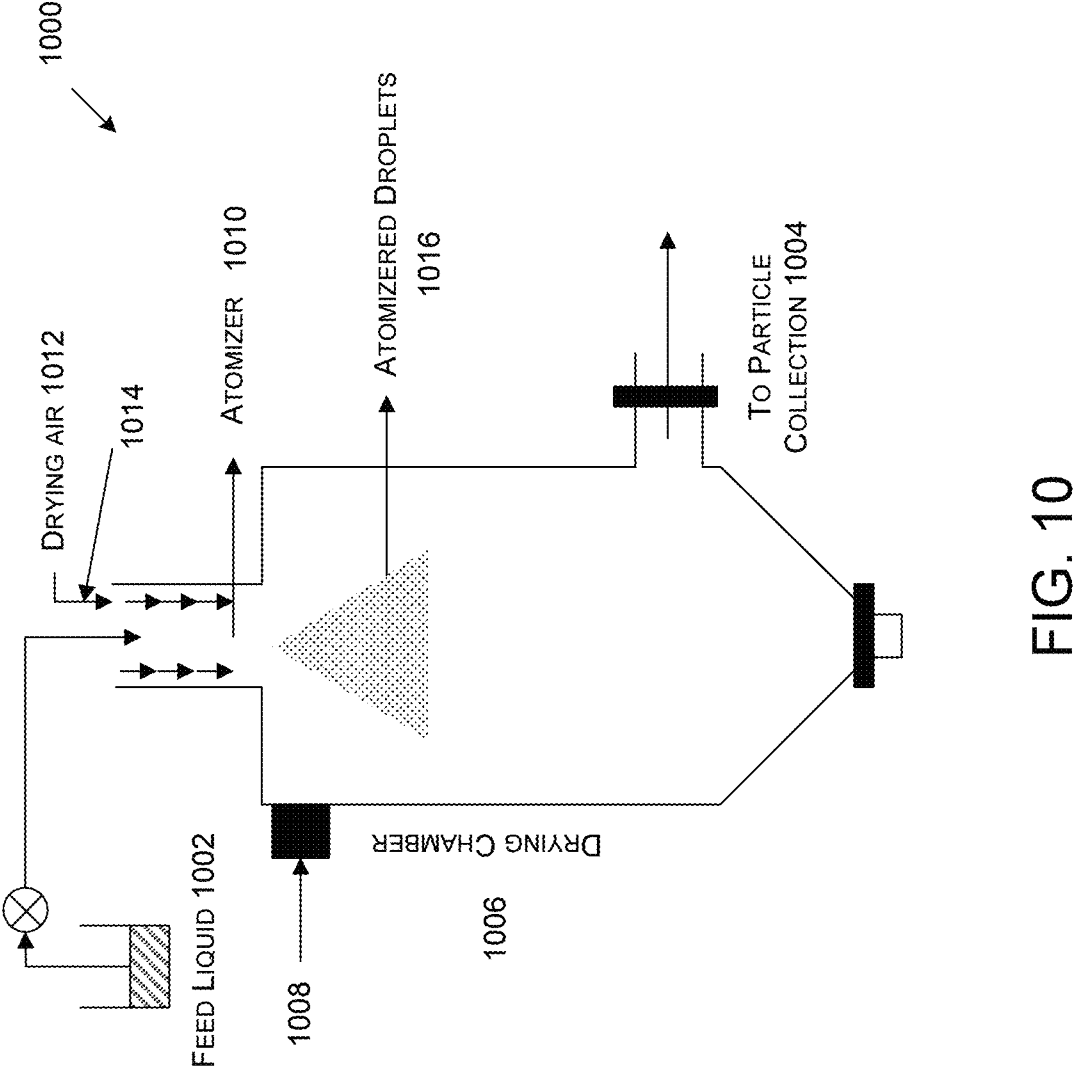
FIG. 10 illustrates a spray dryer system for transforming a liquid-solid suspension feed solution into a desirable output product, in accordance with the present invention.

FIG. 10 illustrates a spray dryer system (1000) for transforming a liquid-solid suspension feed solution (1002) into a desirable output product (1004), in accordance with the present invention. In an embodiment, a drying chamber (1006) having a controller device (1008). The controller device controls the operations of the drying chamber (1006) to obtain the desirable output product.

The controller device is configured to obtain a first input associated with one or more properties of a desirable output product, obtain a second input associated with one or more critical quality attributes (CQAs) of the desirable output product, and obtain a third input associated with one or more operational process variables of the drying chamber to generate the desirable output product.

The drying chamber is adapted to receive dispersed droplets (1016) of a feed solution, wherein the dispersed droplets are generated based on the one or more obtained properties, the one or more obtained CQAs, and the one or more obtained operational process variables, and thereby transforms the dispersed droplets into dry particles by drying the dispersed droplets by supplying a continuous flow of the air for drying, wherein the dry particles are generated based on the one or more obtained properties. The one or more obtained CQAs, and the one or more obtained operational process variables.

In an exemplary embodiment, an automizer (1010) fluidly coupled to the drying chamber to generate the dispersed droplets (1016) from the feed solution to feed to the drying chamber.

In an exemplary embodiment, an air distribution system (1012) coupled to the drying chamber to supply the continuous flow of the air for drying the dispersed droplets. The air distribution system directs the flow of the drying air into the drying chamber with a uniform temperature and a uniform velocity.

In an exemplary embodiment, a heater (1014) for heating the continuous flow of the air entering into the drying chamber for drying the dispersed droplets. The air is heated at a pre-determined temperature so that the heated air entering the drying chamber generates a heated gas atmosphere inside the drying chamber to transform the dispersed droplets into dry particles.

In an exemplary embodiment, the one or more properties are associated with at least one of a hardness, a disintegration time, a friability, and a content uniformity.

In an exemplary embodiment, the one or more critical quality attributes (CQAs) are associated with at least one of a moisture content, a particle size distribution, a stickiness, a bulk density, and a flowability index.

In an exemplary embodiment, the one or more operational process variables are associated with at least one of a feed flow rate, an inlet air temperature of hot air, a feed flow rate of the feed solution, a feed concentration of the feed solution, and an atomiser speed generating the dispersed droplets.

In an illustrative configuration, the controller device (1008) (may be interchangeably referred to as "server" or "an electronic device") may include one or more processors (processor(s)), one or more memory devices (generically referred to herein as memory), one or more input/output (I/O) interface(s), one or more network interface(s), one or more sensors or sensor interface(s), one or more transceivers, one or more optional speakers, one or more optional microphones, and data storage. The remote server may further include one or more buses that functionally couple various components of the remote server. The remote server may further include one or more antenna(e) that may include, without limitation, a cellular antenna for transmitting or receiving signals to/from a cellular network infrastructure, an antenna for transmitting or receiving Wi-Fi signals to/from an access point (AP), a Global Navigation Satellite System (GNSS) antenna for receiving GNSS signals from a GNSS satellite, a Bluetooth antenna for transmitting or receiving Bluetooth signals, a Near Field Communication (NFC) antenna for transmitting or receiving NFC signals, and so forth. These various components will be described in more detail hereinafter.

The bus(es) may include at least one of a system bus, a memory bus, an address bus, or a message bus, and may permit exchange of information (e.g., data (including computer-executable code), signalling, etc.) between various components of the remote server. The bus(es) may include, without limitation, a memory bus or a memory controller, a peripheral bus, an accelerated graphics port, and so forth. The bus(es) may be associated with any suitable bus architecture including, without limitation, an Industry Standard Architecture (ISA), a Micro Channel Architecture (MCA), an Enhanced ISA (EISA), a Video Electronics Standards Association (VESA) architecture, an Accelerated Graphics Port (AGP) architecture, a Peripheral Component Interconnects (PCI) architecture, a PCI-Express architecture, a Personal Computer Memory Card International Association (PCMCIA) architecture, a Universal Serial Bus (USB) architecture, and so forth.

The memory of the remote server may include volatile memory (memory that maintains its state when supplied with power) such as random-access memory (RAM) and/or non-volatile memory (memory that maintains its state even when not supplied with power) such as read-only memory (ROM), flash memory, ferroelectric RAM (FRAM), and so forth. Persistent data storage, as that term is used herein, may include non-volatile memory. In certain example embodiments, volatile memory may enable faster read/write access than non-volatile memory. However, in certain other example embodiments, certain types of non-volatile memory (e.g., FRAM) may enable faster read/write access than certain types of volatile memory.

In various implementations, the memory may include multiple different types of memory such as various types of static random-access memory (SRAM), various types of dynamic random-access memory (DRAM), various types of unalterable ROM, and/or writeable variants of ROM such as electrically erasable programmable read-only memory (EEPROM), flash memory, and so forth. The memory may include main memory as well as various forms of cache memory such as instruction cache(s), data cache(s), translation lookaside buffer(s) (TLBs), and so forth. Further, cache memory such as a data cache may be a multi-level cache organized as a hierarchy of one or more cache levels (L1, L2, etc.).

The data storage may include removable storage and/or non-removable storage including, but not limited to, magnetic storage, optical disk storage, and/or tape storage. The data storage may provide non-volatile storage of computer-executable instructions and other data. The memory and the data storage, removable and/or non-removable, are examples of computer-readable storage media (CRSM) as that term is used herein.

The data storage may store computer-executable code, instructions, or the like that may be loadable into the memory and executable by the processor(s) to cause the processor(s) to perform or initiate various operations. The data storage may additionally store data that may be copied to memory for use by the processor(s) during the execution of the computer-executable instructions. Moreover, output data generated as a result of execution of the computer-executable instructions by the processor(s) may be stored initially in memory, and may ultimately be copied to data storage for non-volatile storage.

More specifically, the data storage may store one or more operating systems (O/S); one or more database management systems (DBMS); and one or more program module(s), applications, engines, computer-executable code, scripts, or the like such as, for example, one or more machine learning module(s), one or more communication module(s), one or more content scanning module(s), and/or one or more prediction module(s). Some or all of these module(s) may be sub-module(s). Any of the components depicted as being stored in data storage may include any combination of software, firmware, and/or hardware. The software and/or firmware may include computer-executable code, instructions, or the like that may be loaded into the memory for execution by one or more of the processor(s). Any of the components depicted as being stored in data storage may support functionality described in reference to correspondingly named components earlier in this disclosure.

The data storage may further store various types of data utilized by components of the remote server. Any data stored in the data storage may be loaded into the memory for use by the processor(s) in executing computer-executable code. In addition, any data depicted as being stored in the data storage may potentially be stored in one or more datastore(s) and may be accessed via the DBMS and loaded in the memory for use by the processor(s) in executing computer-executable code. The datastore(s) may include, but are not limited to, databases (e.g., relational, object-oriented, etc.), file systems, flat files, distributed datastores in which data is stored on more than one node of a computer network, peer-to-peer network datastores, or the like. The datastore(s) may include, for example, purchase history information, user action information, user profile information, a database linking search queries and user actions, and other information.

The processor(s) 104 may be configured to access the memory and execute computer-executable instructions loaded therein. For example, the processor(s) may be configured to execute computer-executable instructions of the various program module(s), applications, engines, or the like of the remote server to cause or facilitate various operations to be performed in accordance with one or more embodiments of the disclosure. The processor(s) may include any suitable processing unit capable of accepting data as input, processing the input data in accordance with stored computer-executable instructions, and generating output data. The processor(s) may include any type of suitable processing unit including, but not limited to, a central processing unit, a microprocessor, a Reduced Instruction Set Computer (RISC) microprocessor, a Complex Instruction Set Computer (CISC) microprocessor, a microcontroller, an Application Specific Integrated Circuit (ASIC), a Field-Programmable Gate Array (FPGA), a System-on-a-Chip (SoC), a digital signal processor (DSP), and so forth. Further, the processor(s) may have any suitable microarchitecture design that includes any number of constituent components such as, for example, registers, multiplexers, arithmetic logic units, cache controllers for controlling read/write operations to cache memory, branch predictors, or the like. The microarchitecture design of the processor(s) may be capable of supporting any of a variety of instruction sets.

It should further be appreciated that the system may include alternate and/or additional hardware, software, or firmware components beyond those described or depicted without departing from the scope of the disclosure. More particularly, it should be appreciated that software, firmware, or hardware components depicted as forming part of the remote server 1000 are merely illustrative and that some components may not be present or additional components may be provided in various embodiments. While various illustrative program module(s) have been depicted and described as software module(s) stored in data storage, it should be appreciated that functionality described as being supported by the program module(s) may be enabled by any combination of hardware, software, and/or firmware. It should further be appreciated that each of the above-mentioned module(s) may, in various embodiments, represent a logical partitioning of supported functionality. This logical partitioning is depicted for ease of explanation of the functionality and may not be representative of the structure of software, hardware, and/or firmware for implementing the functionality. Accordingly, it should be appreciated that functionality described as being provided by a particular module may, in various embodiments, be provided at least in part by one or more other module(s). Further, one or more depicted module(s) may not be present in certain embodiments, while in other embodiments, additional module(s) not depicted may be present and may support at least a portion of the described functionality and/or additional functionality. Moreover, while certain module(s) may be depicted and described as sub-module(s) of another module, in certain embodiments, such module(s) may be provided as independent module(s) or as sub-module(s) of other module (s).

Program module(s), applications, or the like disclosed herein may include one or more software components including, for example, software objects, methods, data structures, or the like. Each such software component may include computer-executable instructions that, responsive to execution, cause at least a portion of the functionality described herein (e.g., one or more operations of the illustrative methods described herein) to be performed.

A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform.

Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, or a report writing language. In one or more example embodiments, a software component comprising instructions in one of the foregoing examples of programming languages may be executed directly by an operating system or other software component without having to be first transformed into another form.

A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Software components may invoke or be invoked by other software components through any of a wide variety of mechanisms. Invoked or invoking software components may comprise other custom-developed application software, operating system functionality (e.g., device drivers, data storage (e.g., file management) routines, other common routines and services, etc.), or third-party software components (e.g., middleware, encryption, or other security software, database management software, file transfer or other network communication software, mathematical or statistical software, image processing software, and format translation software).

Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages, but may invoke software components written in another programming language.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or operations specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or operations specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program module(s), or other data transmitted within a data signal, such as a carrier wave, or other transmission. However, as used herein, CRSM does not include CRCM.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

We claim:

1. A method for transforming a liquid-solid suspension feed solution into an output product, the method comprising:

obtaining, at a controller device of a drying chamber, a first input associated with one or more properties of the output product;

obtaining, at the controller device, a second input associated with one or more critical quality attributes (CQAs) of the output product;

obtaining, at the controller device, a third input associated with one or more operational process variables of the drying chamber to generate the output product;

receiving, in the drying chamber, dispersed droplets of the feed solution, wherein the dispersed droplets are generated based on the one or more obtained properties, the one or more obtained CQAs, and the one or more obtained operational process variables;

transforming, in the drying chamber, the dispersed droplets into dry particles by drying the dispersed droplets by supplying a continuous flow of the air for drying, wherein the dry particles are generated based on the one or more obtained properties, the one or more obtained CQAs, and the one or more obtained operational process variables; and wherein the controller device controls the operations of the drying chamber to obtain the output product.

2. The method as claimed in claim 1, wherein the dispersed droplets of the feed solution are obtained from an atomizer fluidly coupled to the drying chamber.

3. The method as claimed in claim 1, wherein the continuous flow of the air for drying is supplied by an air distribution system coupled to the drying chamber, and wherein the air distribution system directs the flow of the drying air into the drying chamber with a uniform temperature and a uniform velocity.

4. The method as claimed in claim 1, wherein the continuous flow of the air for drying, entering into the drying chamber, is heated at a pre-determined temperature so that the heated air entering the drying chamber generates a heated gas atmosphere inside the drying chamber to transform the dispersed droplets into the dry particles.

5. The method as claimed in claim 1, wherein: the one or more properties are associated with at least one of a hardness, a disintegration time, and a friability; the one or more critical quality attributes (CQAs) are associated with at least one of a moisture content, a particle size distribution, a bulk density, and a flowability index; the one or more operational process variables are associated with at least one of a feed flow rate, an inlet air temperature of hot air, a feed flow rate of the feed solution, a feed concentration of the feed solution, and an atomizer speed generating the dispersed droplets.

6. The method as claimed in claim 1, wherein the output product is a solid unit dosage form of medication with excipients.

7. The method as claimed in claim 1, wherein the method further includes:

obtaining, at an outlet of the drying chamber, the dry particles along with the air for drying;

collecting, at a collection chamber connected to the drying chamber, the obtained dry particles and allowing the obtained air for drying into atmosphere.

* * * * *